United States Patent
Metivier

(10) Patent No.: US 6,184,421 B1
(45) Date of Patent: *Feb. 6, 2001

(54) METHOD FOR PREPARING A 4-HYDROXYBENZALDEHYDE AND DERIVATIVES

(75) Inventor: Pascal Metivier, Sainte Foy les Lyon (FR)

(73) Assignee: Rhodia Chimie, Courbevoie (FR)

( * ) Notice: Under 35 U.S.C. 154(b), the term of this patent shall be extended for 0 days.

This patent is subject to a terminal disclaimer.

(21) Appl. No.: 09/308,065

(22) PCT Filed: Nov. 19, 1997

(86) PCT No.: PCT/FR97/02085

§ 371 Date: May 13, 1999

§ 102(e) Date: May 13, 1999

(87) PCT Pub. No.: WO98/22419

PCT Pub. Date: May 28, 1998

(30) Foreign Application Priority Data

Nov. 22, 1996 (FR) .................................................. 96 14275

(51) Int. Cl.⁷ .................................................. C07C 45/38
(52) U.S. Cl. .................. 568/432; 568/433; 568/442; 568/764; 562/475
(58) Field of Search ..................................... 568/432, 433, 568/424, 442, 764; 562/406, 475, 463

(56) References Cited

U.S. PATENT DOCUMENTS 4,351,962 * 9/1982 Gradeff et al. ........................ 568/432
4,366,325 * 12/1982 Wedemeyer et al. ................. 568/432

FOREIGN PATENT DOCUMENTS

72600 * 3/1893 (DE).
774696 * 5/1957 (GB).

OTHER PUBLICATIONS

Eugenio et al, Farmaco, 46(5), 669–676, 1991.*
Cavina et al, CA, vol. 52, 11776i, 1995.*
Mar., Advanced Organic Chemistry, third edition, p. 507, 1985.*

* cited by examiner

Primary Examiner—Sreeni Padmanabhan
(74) Attorney, Agent, or Firm—Jean-Louis Seugnet

(57) ABSTRACT

The present invention concerns a process for the preparation of a 4-hydroxybenzaldehyde and its derivatives. More particularly, the invention concerns the preparation of 3-methoxy-4-hydroxybenzaldehyde and 3-ethoxy-4-hydroxybenzaldehyde, respectively known as vanillin and ethylvanillin. The process for the preparation of a 4-hydroxybenzaldehyde and its derivatives is characterized in that it consists of selectively oxidising, to a carboxy group, the group in the 2 position with respect to the hydroxyl group, present in the phenolic compounds in a mixture comprising at least a phenolic compound (A) carrying formyl and/or hydroxymethyl groups in the 2 and 4 position, a phenolic compound (B) carrying a formyl or hydroxymethyl group in the 4 position, a phenolic compound (C) carrying a formyl or hydroxymethyl group in the 2 position, resulting in a mixture comprising a 3-carboxy-4-hydroxybenzaldehyde, a 4-hydroxybenzaldehyde and a 2-hydroxybenzoic acid, which then undergoes a decarboxylation operation to produce the 4-hydroxybenzaldehyde and a phenol which can optionally be recycled.

46 Claims, No Drawings

METHOD FOR PREPARING A 4-HYDROXYBENZALDEHYDE AND DERIVATIVES

This application is an application under 35 U.S.C. Section 371 of International Application Number PCT/FR97/02085, filed on Nov. 19, 1997.

The present invention concerns a process for the preparation of a 4-hydroxybenzaldehyde and its derivatives.

More particularly, the invention concerns the preparation of 3-methoxy-4-hydroxybenzaldehyde and 3-ethoxy-4-hydroxybenzaldehyde, respectively known as vanillin and ethylvanillin.

In French patent application n° 95/06186, a process is described for the preparation of 4-hydroxybenzaldehydes, more particularly vanillin and ethylvanillin.

The process described consists of preparing a 3-carboxy-4-hydroxybenzaldehyde then decarboxylating that compound to produce the 4-hydroxybenzaldehyde.

According to FR n°95/06186, the 3-carboxy-4-hydroxybenzaldehyde is prepared from one of the compounds given below and mixtures thereof, more particularly with the following formulae (IIa), (IIb), (IIc) and (IId) given below:

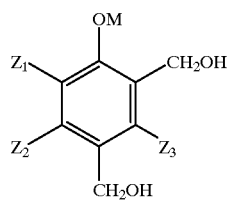
(IIa)

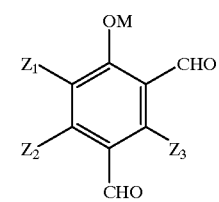
(IIb)

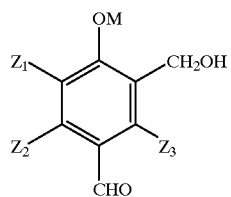
(IIc)

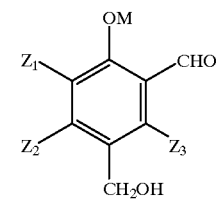
(IId)

where:
M represents a hydrogen atom and/or a metallic cation from group (Ia) or (IIa), or an ammonium cation;
$Z_1$, $Z_2$ and $Z_3$, which may be identical or different, represent a hydrogen atom, an alkyl, alkenyl, alkoxy, hydroxyalkyl, alkoxyalkyl, cycloalkyl or aryl radical, a hydroxyl group, a nitro group, a halogen atom, or a trifluoroethyl group.

In that patented process, the starting compound is a bifunctional phenolic compound carrying two functional groups on the aromatic ring in the ortho and para positions which can be a —CHO group and/or a —CH$_2$OH group.

Firstly, the ortho group is selectively oxidised to a carboxylic group; the group in the para position is at most oxidised to a formyl group. After eliminating the carboxy group in the ortho position, a 4-hydroxybenzaldehyde is obtained.

Thus vanillin and ethylvanillin can advantageously be prepared using a process which is selective and also highly competitive from an industrial viewpoint as it uses inexpensive reactants.

However, in that process it is difficult to obtain a reaction yield (expressed with respect to the starting phenol) of more than 70% as obtaining a high yield of a bifunctional phenolic compound is accompanied by that of a by-product, namely a bis-arylmethane.

During our research, we discovered in French application no96/12479 that a 4-hydroxybenzaldehyde can be prepared from a mixture of monosubstituted phenolic compounds, one (A) carrying a formyl or hydroxymethyl group in the 2 position, and the other (B) carrying a formyl or hydroxymethyl group in the 4 position, and selectively oxidising the formyl or hydroxymethyl group in the 2 position of compound (A) to a carboxy group, and possibly a hydroxymethyl group in the 4 position of compound (B) to a formyl group, thus producing a mixture of a 2-hydroxybenzoic acid and a 4-hydroxybenzaldehyde from which the latter is separated.

More particularly, that mixture of phenolic compounds used has general formula (II):

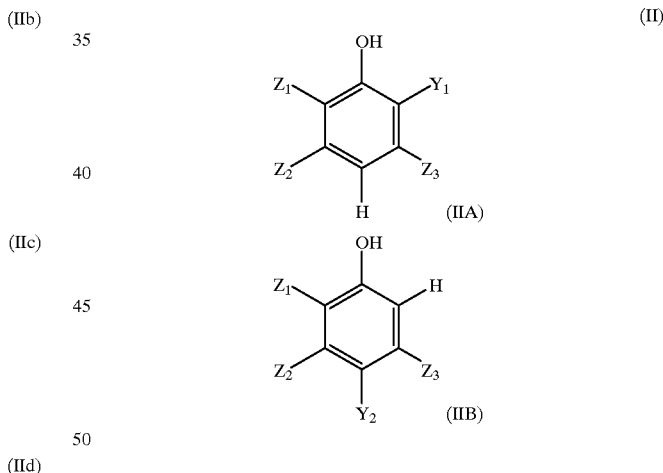

where, in formulae (IIA) and (IIB):
$Y_1$ and $Y_2$, which may be identical or different, represent one of the following groups:
  a —CHO group;
  a CH$_2$OH group;
$Z_1$, $Z_2$ and $Z_3$, which may be identical or different, represent a hydrogen atom, an alkyl, alkenyl, alkoxy, hydroxyalkyl, alkoxyalkyl, cycloalkyl or aryl radical, a hydroxyl group, a nitro group, a halogen atom, or a trifluoroethyl group.

The disadvantage of that process is that to obtain compounds with formula (IIA) or (IIB), by hydroxymethylation of a phenol, it is essential to work with a low degree of conversion of the starting phenol which results in low productivity.

Thus the existing processes must be improved in order to have available a process which is of great economic interest which minimises the by-products and can produce a high operating productivity.

We have discovered, and this constitutes one aspect of the present invention, a process for the preparation of a 4-hydroxybenzaldehyde and its derivatives, characterized in that it consists of selectively oxidising, to a carboxy group, the group in the 2 position with respect to the hydroxyl group, present in the phenolic compounds in a mixture comprising at least:

a phenolic compound (A) carrying formyl and/or hydroxymethyl groups in the 2 and 4 position;

a phenolic compound (B) carrying a formyl or hydroxymethyl group in the 4 position;

a phenolic compound (C) carrying a formyl or hydroxymethyl group in the 2 position;

resulting in a mixture comprising a 3-carboxy-4-hydroxybenzaldehyde, a 4-hydroxybenzaldehyde and a 2-hydroxybenzoic acid, which then undergoes a decarboxylation operation to produce the 4-hydroxybenzaldehyde and a phenol which can optionally be recycled.

In a further aspect, the invention provides a starting mixture of phenolic compounds claimed as the mixture itself, and the mixture obtained after oxidation.

Finally, processes for preparing these mixtures constitute further aspects of the invention.

In the process of the invention, we have discovered that by starting from a mixture of starting compounds as defined above, it is possible to carry out simultaneous intramolecular oxidation (A) and intermolecular oxidation (B+C) since oxidation of the carboxy group takes place preferentially on the hydroxymethyl or formyl group in the ortho position.

The process of the invention thus comprises an oxidation step and a decarboxylation step for a 3-carboxy-4-hydroxybenzaldehyde to a 4-hydroxybenzaldehyde and a 2-hydroxybenzoic acid which can produce the phenolic starting compound which can then be recycled; the 4-hydroxybenzaldehyde is then recovered conventionally.

The starting substrates used in the process of the invention are mixtures of phenolic compounds, one (A) carrying formyl and/or hydroxymethyl groups in the 2 and 4 positions, the second (B) carrying a formyl or a hydroxymethyl group in the 4 position and the last, (C), in the 2 position.

The term "phenolic compound" means any aromatic compound with an aromatic nucleus which carries a hydroxy group.

In the following disclosure of the present invention, the term "aromatic" means the conventional idea of aromaticity as defined in the literature, in particular in "Advanced Organic Chemistry" by Jerry MARCH, 4$^{th}$ edition, John Wiley and Sons, 1992, pp. 40 ff.

Thus a mixture (II) of phenolic compounds is used which, more particularly, have the following formulae:

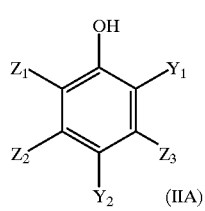

(II)

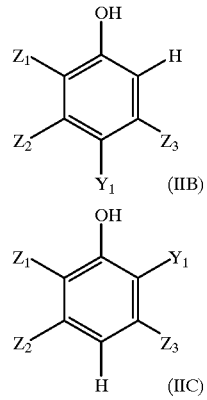

In formulae (IIA) to (IIC):

$Y_1$ and $Y_2$, which may be identical or different, represent one of the following groups:
   a —CHO group;
   a —CH$_2$OH group;

$Z_1$, $Z_2$ and $Z_3$, which may be identical or different, represent a hydrogen atom, an alkyl, alkenyl, alkoxy, hydroxyalkyl, alkoxyalkyl, cycloalkyl or aryl radical, a hydroxy group, a nitro group, a halogen atom, or a trifluoromethyl group.

Particularly suitable compounds for use in the process of the invention have formulae (IIA) to (IIC) where $Z_1$, $Z_2$ and $Z_3$, which may be identical or different, represent one of the following groups:

a hydrogen atom;

a linear or branched alkyl radical containing 1 to 12 carbon atoms, preferably 1 to 4 carbon atoms, such as methyl, ethyl, propyl, isopropyl, butyl, isobutyl, sec-butyl or tert-butyl;

a linear or branched alkenyl radical containing 2 to 12 carbon atoms, preferably 2 to 4 carbon atoms, such as vinyl or allyl;

a linear or branched alkoxy radical containing 1 to 12 carbon atoms, preferably 1 to 4 carbon atoms, such as a methoxy, ethoxy, propoxy, isopropoxy, butoxy, isobutoxy, sec-butoxy or tert-butoxy radical;

a phenyl radical;

a halogen atom, preferably a fluorine, chlorine or bromine atom.

The present invention does not exclude the presence of substituents of different natures on the aromatic ring, provided that they do not interfere with the reactions taking place in the process of the invention.

The present invention is preferably applicable to compounds with formula (IIA) to (IIC) where $Z_1$ represents a hydrogen atom or a linear or branched alkyl or alkoxy radical containing 1 to 6 carbon atoms, preferably 1 to 4 carbon atoms; $Z_2$ and $Z_3$ represent a hydrogen atom; and $Y_1$ and $Y_2$ are identical and represent a formyl group or a hydroxymethyl group.

Preferred examples of mixtures of phenolic compounds for use in the process of the invention are:

o-hydroxymethylguaiacol, p-hydroxymethylguaiacol and 4,6-di(hydroxymethyl)guaiacol;

o-formylguaiacol, p-formylguaiacol and 4,6-diformylguaiacol;

o-hydroxymethylguetol, p-hydroxymethylguetol and 4,6-di(hydroxymethyl)guetol;

o-formylguetol, p-formylguetol and 4,6-diformylguetol.

The process of the invention uses a starting mixture of phenolic compounds which preferably have formula (II).

The proportion of each phenolic compound in the mixture depends on the method of their preparation.

Preferred mixtures comprise:
30% to 70% by weight, more preferably 50% to 70%, of a phenolic compound (A);
30% to 70% by weight, more preferably 50% to 70%, of a mixture of phenolic compounds (B+C).

As an indication, the quantities of isomers B and C are approximately equimolar in the mixture.

A reaction scheme is given below to facilitate comprehension of the disclosure of the invention without in any way limiting the scope of the invention to the scheme.

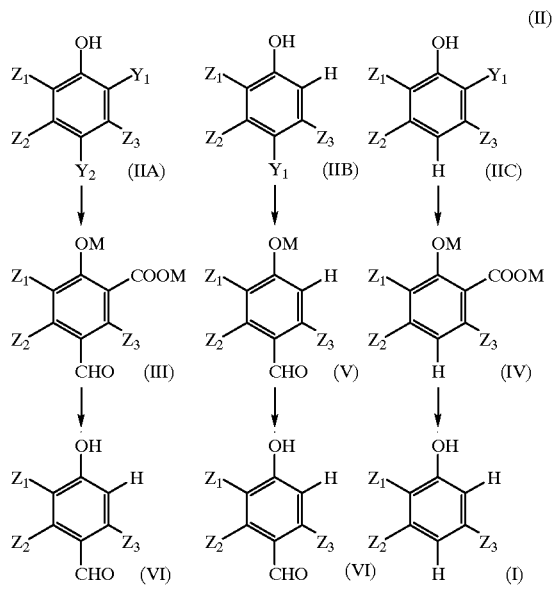

In formulae (I) to (VI):
$Y_1$ and $Y_2$, which may be identical or different, represent one of the following groups:
   a —CHO group;
   a —CH$_2$OH group;
M represents a hydrogen atom and/or a metallic cation from group (Ia) or (IIa) of the periodic table, or an ammonium cation;
$Z_1$, $Z_2$ and $Z_3$, have the meanings given above.

In the present text, reference will be made to the periodic table published in the "Bulletin de la Société Chimique de France", n°1 (1966).

In accordance with the process of the invention, the $Y_1$ group in position 2 of phenolic compounds (A) and (C) preferably with formulae (IIA) and (IIC) is selectively oxidised to a carboxy group, and a hydroxymethyl group, if present in the 4 position in phenolic compounds (A) and (B) preferably with formulae (IIA) and (IIB), is selectively oxidised to a formyl group.

Oxidation is carried out using molecular oxygen or a gas containing molecular oxygen, generally in the presence of a catalyst.

A preferred oxidation method consists of oxidising a mixture of phenolic compounds with formula (II) in the liquid phase using molecular oxygen or a gas containing molecular oxygen, in an aqueous medium comprising a basic agent, in the presence of a catalyst based on a metal $M_1$ selected from metals from group 1b and 8 of the periodic classification of the elements, which may optionally contain, as an activator, metals such as cadmium, cerium, bismuth, lead, silver, tellurium or tin.

We have surprisingly discovered that if the temperature is increased and the reaction is preferably carried out under pressure or if the quantity of base present during oxidation is increased, group $Y_1$ in the 2 position in phenolic compounds (A) and (C), preferably with formulae (IIA) and (IIC) is selectively oxidised to a carboxy group, and the group located in the 4 position in phenolic compounds (A) and (B), preferably with formulae (IIA) and (IIB), is at most oxidised to the formyl group.

The catalysts used in the process of the invention are based on a metal from group 1b and 8 of the periodic classification.

Examples of catalysts based on a metal from group 8 of the periodic classification are nickel, ruthenium, rhodium, palladium, osmium, iridium, platinum and mixtures thereof. Regarding metals from group 1b, copper is preferred.

Preferably, platinum and/or palladium catalysts are used, in any available form such as: platinum black, palladium black, platinum oxide, palladium oxide or the noble metal itself deposited on different supports such as carbon black, calcium carbonate, aluminas or activated silicas or equivalent materials. Catalytic masses based on carbon black are particularly suitable.

The quantity of catalyst used, expressed as the weight of metal $M_1$ with respect to that of the phenolic compound with formula (II), can vary from 0.01% to 10%, preferably 0.04% to 2%.

Further details of the catalysts can be obtained from U.S. Pat. No. 3,673,257, and French patents FR-A-2 305 420 and FR-A2 350 323.

The activator can be selected from all those mentioned in the above patents. Preferably, bismuth, lead and cadmium are used as the free metal or as cations. In the latter case, the associated anion is not critical and all derivatives of these metals can be used. Preferably, bismuth metal or its derivatives is used.

An inorganic or organic bismuth derivative can be used in which the bismuth atom has an oxidation number of more than zero, for example 2, 3, 4 or 5. The residue associated with the bismuth is not critical provided that is satisfies this condition. The activator can be soluble or insoluble in the reaction medium.

Illustrative examples of activators which can be used in the process of the present invention are: bismuth oxides; bismuth hydroxides; salts of inorganic hydracids such as: bismuth chloride, bromide, iodide, sulphide, selenide, or telluride; salts of inorganic oxyacids such as: bismuth sulphite, sulphate, nitrite, nitrate, phosphite, phosphate, pyrophosphate, carbonate, perchlorate, antimonate, arsenate, selenite, or selenate; and salts of oxyacids derived from transition metals such as: bismuth vanadate, niobate, tantalate, chromate, molybdate, tungstate, or permanganate.

Other suitable compounds are the salts of aliphatic or aromatic organic acids such as: bismuth acetate, propionate, benzoate, salicylate, oxalate, tartrate, lactate, or citrate; and phenates such as: bismuth gallate or pyrogallate. These salts and phenates can also be bismuthyl salts.

Other inorganic or organic compounds are binary compounds of bismuth with elements such as phosphorous or arsenic; heteropolyacids containing bismuth and salts thereof; also aliphatic and aromatic bismuthines.

Specific examples are:
oxides: BiO; Bi$_2$O$_3$; Bi$_2$O$_4$; Bi$_2$O$_5$;
hydroxides: Bi(OH)$_3$;
salts of inorganic hydracids: bismuth chloride BiCl$_3$; bismuth bromide BiBr$_3$; bismuth iodide BiI$_3$; bismuth sulphide Bi$_2$S$_3$; bismuth selenide Bi$_2$Se$_3$; bismuth telluride Bi$_2$Te$_3$;

salts of inorganic oxyacids: basic bismuth sulphite $Bi_2(SO_3)_3,Bi_2O_3,5H_2O$; neutral bismuth sulphate $Bi_2(SO_4)_3$; bismuthyl sulphate $(BiO)HSO_4$; bismuthyl nitrite $(BiO)NO_2,0.5H_2O$; neutral bismuth nitrate $Bi(NO_3)_3$, $5H_2O$; double nitrate of bismuth and magnesium $2Bi(NO_3)_3,3Mg(NO_3)_2,24H_2O$; bismuthyl nitrate $(BiO)NO_3$; bismuth phosphite $Bi_2(PO_3H)_3,3H_2O$; neutral bismuth phosphate $BiPO_4$; bismuth pyrophosphate $Bi_4(P_2O_7)_3$; bismuthyl carbonate $(BiO)_2CO_3;0.5H_2O$; neutral bismuth perchlorate $Bi(ClO_4)_3,5H_2O$; bismuthyl perchlorate $(BiO)ClO_4$; bismuth antimonate $BiSbO_4$; neutral bismuth arsenate $Bi(AsO_4)_3$; bismuthyl arsenate $(BiO)AsO_4$, $5H_2O$; bismuth selenite $Bi_2(SeO_3)_3$;

salts of oxyacids derived from transition metals: bismuth vanadate $BiVO_4$; bismuth niobate $BiNbO_4$; bismuth tantalate $BiTaO_4$; neutral bismuth chromate $Bi_2(CrO_4)$; bismuthyl dichromate $([BiO]_2Cr_2O_7$; acid bismuthyl chromate $H(BiO)CrO_4$; double chromate of bismuthyl and potassium $K(BiO)CrO_4$; bismuth molybdate $Bi_2(MoO_4)_3$; bismuth tungstate $Bi_2(WO_4)_3$; double molybdate of bismuth and sodium $NaBi(MoO_4)_2$; basic bismuth permanganate $Bi_2O_2(OH)MnO_4$;

salts of aliphatic or aromatic organic acids: bismuth acetate $Bi(C_2H_3O_2)_3$; bismuthyl propionate $(BiO)C_3H_5O_2$; basic bismuth benzoate $C_6H_5CO_2Bi(OH)_2$; bismuthyl salicylate $C_6H_4CO_2(BiO)(OH)$; bismuth oxalate $(C_2O_4)_3Bi_2$; bismuth tartrate $Bi_2(C_4H_4O_6)_3,6H_2O$; bismuth lactate $(C_6H_9O_5)OBi,7H_2O$; bismuth citrate $C_6H_5O_7Bi$;

phenates: basic bismuth gallate $C_7H_7O_7Bi$; basic bismuth pyrogallate $C_6H_3(OH)_2(OBi)(OH)$.

Other inorganic or organic compounds are also suitable: bismuth phosphide BiP; bismuth arsenide $Bi_3As_4$; sodium bismuthate $NaBiO_3$; bismuth-thiocyanic acids $H_2[Bi(BNS)_5],H_3[Bi(CNS)_6]$ and sodium and potassium salts thereof; trimethylbismuthine $Bi(CH_3)_3$, triphenylbismuthine $Bi(C_6H_5)_3$.

Preferred bismuth derivatives for use in the process of the invention are: bismuth oxides; bismuth hydroxides; bismuth or bismuthyl salts of inorganic hydracids; bismuth or bismuthyl salts of inorganic oxyacids; bismuth or bismuthyl salts of aliphatic or aromatic organic acids; and bismuth or bismuthyl phenates.

A particularly suitable group of activators for carrying out the process of the invention is constituted by: bismuth oxides $Bi_2O_3$ and $Bi_2O_4$; bismuth hydroxide $Bi(OH)_3$; neutral bismuth sulphate $Bi_2(SO_4)_3$; bismuth chloride $BiCl_3$; bismuth bromide $BiBr_3$; bismuth iodide $BiI_3$; neutral bismuth nitrate $Bi(NO_3)_3,5H_2O$; bismuthyl nitrate $BiO(NO_3)$; bismuthyl carbonate $(BiO)_2CO_3,0.5H_2O$; bismuth acetate $Bi(C_2H_3O_2)_3$; and bismuthyl salicylate $C_6H_4CO_2(BiO)(OH)$.

The quantity of activator used, expressed as the quantity of metal contained in the activator with respect to the weight of metal $M_1$ used, can be varied between wide limits. As an example, this quantity can be as low as 0.1% and can attain the weight of metal $M_1$ used, or even exceed it without any problems.

More particularly, this quantity is selected so that it provides the oxidation medium with 10 ppm to 900 ppm by weight of activator metal with respect to the phenolic compound with formula (II). In this respect, higher quantities of activator of the order of 900 ppm to 1500 ppm can naturally be used, but with no great additional advantage.

In the process of the invention, oxidation is carried out in an aqueous medium containing a basic agent in solution, more particularly ammonium hydroxide, alkaline or alkaline-earth bases, for example hydroxides such as sodium, potassium, lithium and baryte hydroxides; alkaline alkanolates such as sodium or potassium methylate, ethylate, isopropylate or t-butylate, sodium or potassium carbonates or bicarbonates and in general, the salts of alkaline or alkaline-earth bases and weak acids.

Thus compounds with formulae (III) to (V) can be completely or partially in their salt form depending on the quantity of basic agent used. It follows that in these formulae, M, the residue of the base, generally symbolises a hydrogen atom and/or a metallic cation from group (Ia) or (IIa) or an ammonium cation.

Sodium or potassium hydroxide is used for reasons of economy. The proportion of inorganic base to be used can be in the range 0.5 to 10 moles, preferably in the range 1 to 4 moles, more preferably in the range 2 to 4 moles, of inorganic base per mole of phenolic compounds with formula (II).

The concentration by weight of the mixture of phenolic compounds with formula (II) in the liquid phase is usually in the range 1% to 60%, preferably in the range 2% to 30%.

In practice, one implementation of the process consists of bringing the solution comprising the mixture of phenolic compounds with formula (II), the basic agent, the catalyst based on metal $M_1$, and any activator into contact with molecular oxygen or a gas containing molecular oxygen in the proportions indicated above.

Atmospheric pressure can be used, but it is preferable to operate at a pressure of 1 to 20 bar.

The mixture is then stirred at the desired temperature until a quantity of oxygen has been consumed which corresponds to that necessary to transform the hydroxymethyl group or formyl group of compounds (A) and (C) into a carboxy group, and the hydroxymethyl group, if present in compounds (A) and (B), into a formyl group.

The reaction temperature to be used depends on the thermal stability of the products to be prepared.

In accordance with the invention, the temperature is preferably selected so as to be in the range 30° C. to 200° C., preferably in the range 40° C. to 160° C.

The temperature can be adapted to the reaction conditions by the skilled person (in particular the quantity of base, nature of metal $M_1$, pressure and stirring). In particular, it has been discovered that the lower the temperature the higher must be the quantity of basic agent used.

Examples of preferred conditions in the case of preferred metals platinum and palladium will now be given. For platinum, the temperature can be between 60° C. and 160° C., the quantity of base to be used is advantageously in the range 1 to 3 moles per mole of phenolic compounds with formula (II). For palladium, the temperature can be between 30° C. and 200° C., preferably between 30° C. and 150° C., and for the latter interval, the quantity of base is preferably 2 to 4 moles per mole of phenolic compounds.

The quantity of base must be sufficient to oxidise the $Y_1$ group in the position ortho to the carboxy group. It is determined by the skilled person depending on the temperature and the selected metal.

At the end of the reaction, which preferably takes 30 minutes to 6 hours, a mixture comprising a 3-carboxy-4-hydroxybenzaldehyde preferably with formula (III), a 4-hydroxybenzaldehyde preferably with formula (V) and a 2-hydroxybenzoic acid preferably with formula (IV) are recovered: the compounds can be partially or totally in their salt form.

After any necessary cooling, the catalytic mass and the reaction mass are separated, for example by filtering.

In a second step of the process of the invention, the reaction medium undergoes a decarboxylation reaction.

This is carried out by acidifying the resulting medium by adding a protonic mineral acid, preferably hydrochloric acid or sulphuric acid or an organic acid such as trifluoromethanesulphonic acid or methanesulphonic acid, to obtain a pH 3 or less.

The concentration of acid is immaterial and preferably, commercially available concentrations are used.

The reaction medium is heated to a temperature of between 120° C. and 350° C., preferably between 150° C. and 220° C.

The process is preferably carried out under autogenous pressure of the reactants.

At the end of the reaction, the reaction medium is cooled to between 20° C. and 80° C.

A two-phase medium is obtained constituted by an organic phase comprising the 4-hydroxybenzaldehyde preferably with formula (VI) and the starting phenolic compound with formula (I), and also a saline aqueous phase.

The organic and aqueous phases are separated and the 4-hydroxybenzaldehyde is recovered from the organic phase using conventional separation techniques, for example extraction using an appropriate solvent (for example methylisobutylketone or isopropyl ether), or by distillation.

The improved process of the invention starts with a mixture of two phenolic compounds, one carrying a formyl or hydroxymethyl group in the 2 and 4 position and the two others carrying a formyl or hydroxymethyl group in the 2 or 4 position.

More particularly, the starting mixtures have the formulae given below:

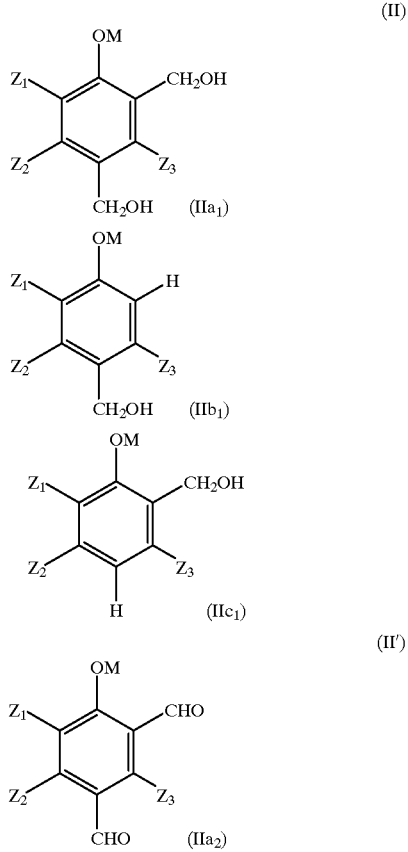

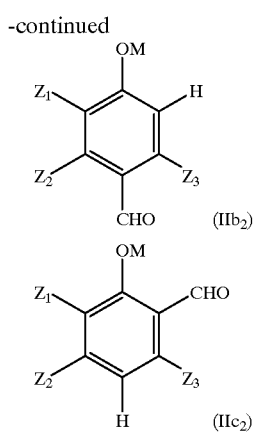

in which formulae:
M represents a hydrogen atom and/or a metallic cation from group (Ia) or group (IIa), or an ammonium cation;
$Z_1$, $Z_2$, $Z_3$ have the meanings given above.

The mixtures of phenolic compounds, to which the process of the invention can be applied, are prepared by a process which constitutes a further aspect of the invention.

Thus mixtures of phenolic compounds with formulae $(IIa_1)$ to $(IIc_1)$ can be obtained by a process for hydroxymethylating a phenol by condensing it with formaldehyde or a formaldehyde generator in an aqueous phase in the presence of and alkaline or alkaline-earth base, so that the phenol conversion is at most 95% optionally followed by an oxidation step.

More precisely, a phenol is used which is not substituted in the ortho and para positions to the hydroxy group, with general formula (I):

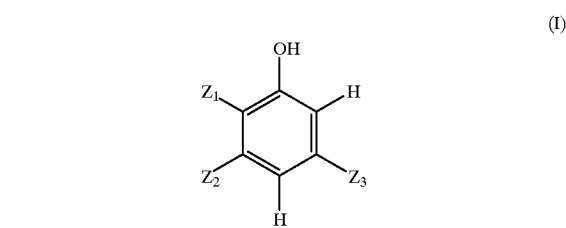

where $Z_1$, $Z_2$ and $Z_3$ have the meanings given above.

Examples of phenols with formula (I) which can act as a starting point for the synthesis of compounds with formula (II) are guaiacol, guetol, 3-methoxyphenol, 3-ethoxyphenol, 3-isopropoxyphenol, 3-t-butoxyphenol, m-cresol and p-cresol.

The conditions selected for carrying out this hydroxymethylation step are those recommended by the prior art listed below: cf in particular H. G. PEER, Rec. Trav. Chim. Netherlands 79, 825–835 (1960); GB-A-774 696; GB-A-751 845; EP-A-165; J. H. FREEMAN, J. Am. Chem. Soc. 74, 6 257–6 260 (1952); and 76 2080–2087 (1954); H. G. PEER, Rec. Trav. Chim. Netherlands 78 851–863 (1959); H. EULER et al., Arkiv für Chem. 13, 1–7 (1939); P. CLAUS et al., Monath. Chem. 103, 1178–11293 (1972).

Formaldehyde or any formaldehyde generator can be used, such as trioxane or paraformaldehyde used as linear paraformaldehydes of any degree of polymerisation, preferably containing 8 to 100 ($CH_2O$) units.

Formaldehyde can be used as an aqueous solution in a concentration which is not critical. It can be in the range 20% to 50% by weight: preferably, commercial solutions are used which have a concentration of about 30% to 40% by weight.

The quantity of formaldehyde, expressed as moles of formaldehyde per mole of phenol, can vary between wide limits. The formaldehyde/phenol molar ratio can be between 1.0 and 4.0, preferably between 1.0 and 2.5.

The quantity of base present in the hydroxymethylation medium, expressed as the number of moles of base/phenolic hydroxy group of the phenol to be hydroxymethylated, can vary between wide limits. In general, this ratio, which varies depending on the base, can be between 1.0 and 4.0, preferably between 0.9 and 2.0. The base used may be one of those cited above for the oxidation step. Aqueous solutions of alkaline hydroxides are particularly suitable.

In general, the hydroxymethylation step is carried out at a temperature in the range 0° C. to 100° C., preferably in the range 20° C. to 70° C.

The process is preferably carried out at a pressure which is autogenous for the reactants to avoid any paraformaldehyde losses which may be gaseous at the temperatures used.

Preferably, the reaction is carried out in a controlled atmosphere of inert gas such as nitrogen or a noble gas, for example argon.

The reaction time can readily be determined by the skilled person depending on the desired degree of conversion of the starting phenol and taking into account the necessity to minimise by-products such as bis-arylmethane. It is usually between 15 minutes and 4 hours, preferably between 1 hour and 3 hours.

The degree of conversion of phenol is controlled by different parameters (temperature, duration, quantity of reactants). It is advantageously in the range 60% to 95%, preferably in the range 80% to 95%.

In practice, the reaction is readily carried out by charging the phenol and formaldehyde, and any base into the apparatus, then stirring and heating the reaction mixture to the desired temperature for the time required to complete the reaction.

The order of introduction of the reactants is not critical and can thus be different.

A mixture of phenolic compounds with formula (IIa$_1$) to (IIc$_1$) is obtained.

Compounds with formula (IIa$_2$) to (IIc$_2$) can be prepared by oxidising hydroxymethylated phenolic compounds with formula (IIa$_1$) to (IIc$_1$), by oxidising using molecular oxygen or a gas containing molecular oxygen, in an aqueous alkaline phase, in the presence of a catalyst based on a metal from group 8 of the periodic table, preferably platinum or palladium, optionally containing metals such as cadmium, cerium, bismuth, lead, silver, tellurium or tin as an activator. Such processes have been described in U.S. Pat. No. 3,673, 257, FR-A-2 305 420 and FR-A-2 350 323.

If necessary, the pH of the solution can be raised to a value in the range 8 to 13 by optional addition of an alkaline or alkaline-earth base. The optional value of the pH depends on the nature of the hydroxymethylated phenols.

The temperature of the oxidation reaction is between 10° C. and 100° C., preferably between 20° C. and 60° C.

More specifically again, the process of the present invention is suitable for the preparation of compounds with formulae (IIa$_2$) to (IIc$_2$) from phenolic compounds with formulae (IIa$_1$) to (IIc$_1$) resulting from the first step, using molecular oxygen or a gas containing molecular oxygen, in the presence of a catalyst based on a metal from group 8 of the periodic table, optionally containing a metal such as those used as an activator, without intermediate separation of the hydroxymethylated phenolic compounds.

From an industrial viewpoint, it is particularly advantageous when carrying out the process of the present invention to use compounds with formula (IIa$_2$) to (IIc$_2$) obtained by a two-step process comprising:

hydroxymethylation of a phenol in an aqueous medium in the presence of an alkaline or alkaline-earth base using formaldehyde or a formaldehyde generator, resulting in a mixture of hydroxymethylated phenolic compounds, one being hydroxymethylated in the 2 and 4 positions and the two others being hydroxymethylated in the 2 or in the 4 position;

and oxidation, without intermediate separation, of the phenolic compounds obtained using molecular oxygen or a gas containing molecular oxygen, in an aqueous alkaline phase in the presence of a catalyst based on a metal from group 8 of the periodic table, and optionally, a metal such as those cited above, acting as an activator.

An additional advantage of the process of the invention is that it allows mixtures of phenolic compounds issuing directly from the preceding hydroxymethylation and optional oxidation steps to be used.

As mentioned above, the process of the invention is particularly suitable for the preparation of vanillin and ethylvanillin from a mixture of phenolic compounds obtained by hydroxymethylation of guaiacol or guetol.

Thus vanillin can be prepared by selectively oxidising a mixture of phenolic compounds, 4,6-di(hydroxymethyl) guaiacol (A), p-hydroxymethylguaiacol (B) and o-hydroxymethylguaiacol (C) at the hydroxymethyl group in the 2-position of compounds (A) and (C) to a carboxy group, and the hydroxymethyl group in the 4 position in compounds (A) and (B) to a formyl group, resulting in a mixture of 3-carboxy-4-hydroxy-5-methoxybenzaldehyde, vanillin and 2-hydroxy-3-methoxybenzoic acid which, after decarboxylation, produces vanillin and guaiacol which can be recycled.

A variation consists of selectively oxidising a mixture of phenolic compounds, 4,6-di(formyl)guaiacol (A), p-formylguaiacol (B) and o-formylguaiacol (C) at the formyl group in the 2-position of compounds (A) and (C) to a carboxy group, resulting in a mixture of 3-carboxy-4-hydroxy-5-methoxybenzaldehyde, vanillin and 2-hydroxy-3-methoxybenzoic acid which, after decarboxylation, produces vanillin and guaiacol which can be recycled.

Ethylvanillin is prepared by the process of the present invention by selectively oxidising a mixture of phenolic compounds, 4,6-di(hydroxymethyl)guetol (A), p-hydroxymethylguetol (B) and o-hydroxymethylguetol (C) at the hydroxymethyl group in the 2-position of compounds (A) and (C) to a carboxy group, and the hydroxymethyl group in the 4 position in compounds (A) and (B) to a formyl group, resulting in a mixture of 3-carboxy-4-hydroxy-5-ethoxybenzaldehyde, ethylvanillin and 2-hydroxy-3-ethoxybenzoic acid which, after decarboxylation, produces ethylvanillin and guetol which can be recycled.

A further variation consists of selectively oxidising a mixture of phenolic compounds, 4,6-di(formyl)guetol (A), p-formylguetol (B) and o-formylguetol (C) at the formyl group in the 2-position of compounds (A) and (C) to a carboxy group, resulting in a mixture of 3-carboxy-4-hydroxy-5-ethoxybenzaldehyde, ethylvanillin and 2-hydroxy-3-ethoxybenzoic acid which, after decarboxylation, produces vanillin and guaiacol which can be recycled.

Examples of implementations of the invention will now be given. These examples are given by way of indication and are in no way limiting.

The degree of conversion and the yield obtained are defined in the examples.

The degree of conversion (TT) corresponds to the ratio between the number of moles of substrate transformed and the number of moles of substrate used.

The yield (RR) corresponds to the ratio between the number of moles of product formed and the number of moles of substrate used.

The yield ($RT_{vanillin}$) corresponds to the ratio between the number of moles of vanillin formed and the number of moles of guaiacol transformed in the sequence.

The following abbreviations are used in the examples:
o-hydroxymethylguaiacol=OMG
p-hydroxymethylguaiacol=PMG
o-vanillin=3-methoxy-2-hydroxybenzaldehyde=OVA
p-vanillin=3-methoxy-4-hydroxybenzaldehyde=PVA
o-vanillic acid=2-hydroxy-3-methoxybenzoic acid=AOV
p-vanillic acid=4-hydroxy-3-methoxybenzoic acid=APV
4,6-di(hydroxymethyl) guaiacol=DMG
4,3-(diformyl)guaiacol=DFG
o-carboxyvanillin=OCVA
4,6-(dicarboxy)guaiacol=DCG.

EXAMPLE 1

1. Condensation Step

The following was charged into a 2 liter reactor provided with a mechanical stirrer and a temperature regulation means:
152 g of guaiacol;
249 g of an aqueous 30% formol solution;
49.2 g of caustic soda;
872 g of water.

The reaction medium was kept at 45° C. for 1 hour then cooled and analysed using high performance liquid chromatography.

The reaction balance was as follows:
guaiacol conversion=90%
o-hydroxymethyl guaiacol (OMG) yield=15%
p-hydroxymethyl guaiacol (PMG) yield=18%
4,6-di(hydroxymethyl) guaiacol (DMG) yield=83%

The sum of the upgradable products was 93%.

2. Oxidation Step

The reaction medium was then diluted with 1500 g of water and 148 g of caustic soda.

The reaction medium was then introduced into a 3.9 liter autoclave provided with a self exhausting turbine.

0.54 g of bismuth trioxide and 22 g of a palladium catalyst deposited on carbon black in a proportion of 3% by weight of metal were then added.

Stirring was started at a rate of 1500 rpm and the temperature of the reaction medium was raised to 45° C. under nitrogen. It was then placed under a pressure of 3 bars and air was introduced into the reaction medium at a rate of 300 g/h. The reaction medium was held under these conditions for 6 hours.

The reaction medium was cooled and the pressure was reduced to atmospheric pressure then the catalyst was filtered.

The reaction medium was then analysed by high performance liquid chromatography.

The yields were as follows (for the complete sequence):
TT guaiacol=92%
ortho series
  RR o-hydroxymethyl guaiacol (OMG)=0%
  RR orthovanillin (OVA)=1%
  RR orthovanillic acid (AOV)=14%
para series
  RR p-hydroxymethylguaiacol (PMG)=0%
  RR vanillin (PVA)=16%
  RR para-vanillic acid (APV)=1%
di series
  RR 4,6-di(hydroxymethyl) guaiacol (DMG)=0%
  RR 4,6-(diformyl) guaiacol (DFG)=1%
  RR orthocarboxyvanillin (OCVA)=47%
  RR 4,6-(dicarboxy) guaiacol (DCG)=10%

The sum of the yields of the upgradable products (guaiacol+OAV+PVA+APV+OCVA+DCG) was 87%.

3. Decarboxylation of Reaction Mixture 199.91 g of this reaction mixture was neutralised with 16.69 g of 92% sulphuric acid and introduced into a 300 ml autoclave provided with a turbine and a temperature regulation system.

The reaction medium was heated to 175° C. for 3 hours under autogenous pressure then cooled and measured using liquid chromatography.

The vanillin yield and the guaiacol conversion were as follows:
TT guaiacol=76%/initial guaiacol
RR vanillin=61%/initial guaiacol, i.e., RT vanillin=80%

EXAMPLE 2

1. Condensation Step

The following was charged into a 2 liter reactor provided with a mechanical stirrer and a temperature regulation means:
133 g of guaiacol;
202 g of an aqueous 30% formol solution;
145 g of an aqueous 30% caustic soda solution;
480 g of water.

The reaction medium was kept at 47° C. for 0 h 50 then cooled 290 g of an aqueous 30% caustic soda solution was added. It was analysed using high performance liquid chromatography. The reaction balance was as follows:
guaiacol conversion=97%
o-hydroxymethyl guaiacol (OMG) yield=10%
p-hydroxymethyl guaiacol (PMG) yield=12%
4,6-di(hydroxymethyl) guaiacol (DMG) yield=70%
(OMG+DMG+PMG) yields=92%

The sum of the RT yields of the upgradable products was 95%.

2. Oxidation Step

The reaction medium was then diluted with 1230 g of water

The reaction medium was introduced into a 3.9 liter autoclave provided with a self exhausting turbine.

0.54 g of bismuth trioxide and 34.5 g of a platinum catalyst deposited on carbon black in a proportion of 2% by weight of metal were then added.

Stirring was started at a rate of 950 rpm and the temperature of the reaction medium was raised to 70° C. under nitrogen. It was then placed under a pressure of 4 bars and air was introduced into the reaction medium at a rate of 200 g/h. The reaction medium was held under these conditions for 5 hours.

The reaction medium was cooled and the pressure was reduced to atmospheric pressure then the catalyst was filtered.

The reaction medium was then analysed by high performance liquid chromatography.

The yields were as follows (for the complete sequence):
TT guaiacol=97%
ortho series
  RR o-hydroxymethyl guaiacol (OMG)=0%
  RR orthovanillin (OVA)=1%

RR orthovanillic acid (AOV)=6%
para series
  RR p-hydroxymethylguaiacol (PMG)=0%
  RR vanillin (PVA)=9%
  RR para-vanillic acid (APV)=2%
di series
  RR 4,6-di(hydroxymethyl) guaiacol (DMG)=0%
  RR 4,6-(diformyl) guaiacol (DFG)=1%
  RR orthocarboxyvanillin (OCVA)=54%
  RR 4,6-(dicarboxy) guaiacol (DCG)=6%.

The sum of the yields of the upgradable products (guaiacol+OAV+PVA+APV+OCVA+DCG) was 80%.

3. Decarboxylation of Reaction Mixture 150 g of this reaction mixture was neutralised with 15 ml of 10 mol/l sulphuric acid and introduced into a 300 ml autoclave provided with a turbine and a temperature regulation system.

The reaction medium was heated to 175° C. for 2 hours under autogenous pressure then cooled and measured using liquid chromatography.

The vanillin yield and the guaiacol conversion were as follows:
TT guaiacol=91%/initial guaiacol
RR vanillin=52%/initial guaiacol, i.e., RT vanillin=57%

What is claimed is:

1. A process for the preparation of a 4-hydroxybenzaldehyde and its derivatives, comprising the steps of:

a) selectively oxidizing, to a carboxy group, the group in the 2 position with respect to the hydroxyl group, present in a starting mixture of phenolic compounds comprising at least:
    a phenolic compound (A) carrying formyl and/or hydroxymethyl groups in the 2 and 4 position;
    a phenolic group (B) carrying a formyl or hydroxymethyl group in the 4 position; and
    a phenolic compound (C) carrying a formyl or hydroxymethyl group in the 2 position;
  resulting in a mixture comprising a 3-carboxy-4-hydroxybenzaldehyde, a 4-hydroxybenzaldehyde and a 2-hydroxybenzoic acid,
  b) carrying out a decarboxylation operation on said resulting mixture obtained in step a) to produce the 4-hydroxybenzaldehyde and a phenol, and
  c) optionally, recycling the phenol obtained in step b).

2. A process according to claim 1, wherein the mixture of phenolic compounds of step a) has general formula (II):

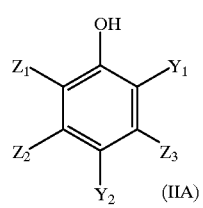

(II)

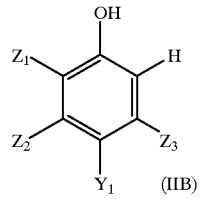

(IIB)

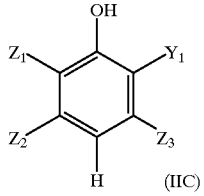

(IIC)

wherein, in formulae (IIA) to (IIC):
  $Y_1$ and $Y_2$, which are identical or different, represent a —CHO group or a —CH$_2$OH group;
  $Z_1$, $Z_2$ and $Z_3$, which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group.

3. A process according to claim 2, wherein the phenolic compounds have formulae (IIA) to (IIC) wherein $Z_1$, $Z_2$ and $Z_3$, which are identical or different, represent a hydrogen atom, a linear alkyl radical containing 1 to 12 carbon atoms, a branched alkyl radical containing 1 to 12 carbon atoms, a linear alkenyl radical containing 2 to 12 carbon atoms, a branched alkenyl radical containing 2 to 12 carbon atoms, a linear alkoxy radical containing 1 to 12 carbon atoms, a branched alkoxy radical containing 1 to 12 carbon atoms, a phenyl radical, or a halogen atom.

4. A process according to claim 3, wherein $Z_1$, $Z_2$ and $Z_3$, which are identical or different, represent methyl, ethyl, propyl, isopropyl, butyl, isobutyl, sec-butyl, tert-butyl, vinyl, allyl, methoxy, ethoxy, propoxy, isopropoxy, butoxy, isobutoxy, sec-butoxy, tert-butoxy, fluorine, chlorine or bromine atom.

5. A process according to claim 2, wherein the phenolic compounds have formulae (IIA) to (IIC), wherein $Z_1$ represents a linear alkyl, a branched alkyl or an alkoxy radical containing 1 to 6 carbon atoms; $Z_2$ and $Z_3$ represent a hydrogen atom; and $Y_1$ and $Y_2$ are identical and represent a formyl group or a hydroxymethyl group.

6. A process according to claim 2, wherein the mixture of phenolic compounds with formula (II) is:
  o-hydroxymethylguaiacol, p-hydroxymethylguaiacol and 4,6-di(hydroxymethyl)guaiacol;
  o-formylguaiacol, p-formylguaiacol and 4,6-diformylguaiacol;
  o-hydroxymethylguetol, p-hydroxymethylguetol and 4,6-di(hydroxymethyl)guetol; and
  o-formylguetol, p-formylguetol and 4,6-diformylguetol.

7. A process according to claim 2, wherein in step a), the mixture of phenolic compounds with formula (II) is oxidized in the liquid phase using molecular oxygen or a gas containing molecular oxygen, in an aqueous medium comprising a basic agent, in the presence of a catalyst comprising a metal $M_1$ from group 1b and 8 of the periodic classification of the elements, said catalyst optionally containing, as an activator, a metal selected from the group consisting of cadmium, cerium, bismuth, lead, silver, tellurium and tin.

8. A process according to claim 7, wherein the catalyst is copper, nickel, ruthenium, rhodium, palladium, osmium, iridium, or platinum.

9. A process according to claim 8, wherein the catalyst is platinum or palladium in the form of platinum black, palladium black, platinum oxide, palladium oxide or platinum or palladium itself deposited on a support.

10. A process according to claim 8, wherein the support is carbon black, calcium carbonate, aluminas or activated silicas.

11. A process according to claim 7, wherein the quantity of catalyst used, expressed as the weight of metal $M_1$ with respect to that of the phenolic compound with formula (II), is from 0.01% to 10%.

12. A process according to claim 7, wherein the catalyst further comprises an activator which is an organic or inorganic bismuth derivative selected from the group consisting of bismuth oxides; bismuth hydroxides; bismuth or bismuthyl salts of inorganic hydracids, bismuth or bismuthyl salts of inorganic oxyacids, bismuth or bismuthyl salts of aliphatic or aromatic organic acids; and bismuth or bismuthyl phenates.

13. A process according to claim 12, wherein the bismuth derivative is bismuth oxide $Bi_2O_3$, bismuth oxide $Bi_2O_4$; bismuth hydroxide $Bi(OH)_3$; bismuth chloride $BiCl_3$; bismuth bromide $BiBr_3$; bismuth iodide $BiI_3$; neutral bismuth sulphate $Bi_2(SO_4)_3$; neutral bismuth nitrate $Bi(NO_3)_3,5H_2O$; bismuthyl nitrate $BiO(NO_3)$; bismuthyl carbonate $(BiO)_2CO_3,0.5H_2O$; bismuth acetate $Bi(C_2H_3O_2)_3$ or bismuth salicylate $C_6H_4CO_2(BiO)OH$.

14. A process according to claim 13, wherein the quantity of activator is selected so that the medium contains at least 0.1% by weight of metal activator with respect to the weight of metal $M_1$ used, and 10 to 900 ppm by weight of metal $M_1$ with respect to the mixture of phenolic compounds with formula (II).

15. A process according to claim 7, wherein step a) is carried out within a temperature range of 30° C. to 200° C.

16. A process according to claim 15, wherein step a) is carried out within a temperature range of 40° C. and 160° C.

17. A process according to claim 7, wherein step a) is carried out at a pressure of 1 to 20 bar.

18. A process according to claim 7, wherein step a) is carried out in an aqueous medium containing, in solution, a basic agent in a quantity such that it represents 0.5 to 10 moles of basic agent per mole of phenolic compounds with formula (II).

19. A process according to claim 18, wherein the basic agent is sodium hydroxide or potassium hydroxide in a quantity such that it represents 2 to 4 moles, of basic agent per mole of phenolic compounds with formula (II).

20. A process according to claim 18, wherein step a) is carried out with a platinum catalyst at a temperature of between 60° C. and 160° C.; the quantity of base being in the range 1 to 3 moles per mole of phenolic compounds with formula (II).

21. A process according to claim 18, wherein step a) is carried out with a palladium catalyst at a temperature of between 30° C. and 200° C., the quantity of base being in the range 2 to 4 moles per mole of phenolic compounds with formula (II).

22. A process according to claim 1, wherein the reaction mixture obtained in step a) comprises a 3-carboxy-4-hydroxybenzaldehyde, a 2-hydroxybenzoic acid, and a 4-hydroxybenzaldehyde which are completely or partially in their salt form.

23. A process according to claim 1, wherein the mixture to be decarboxylated in step b) comprises acids of the following formula:

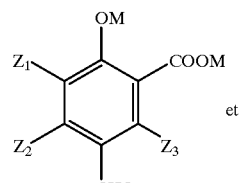

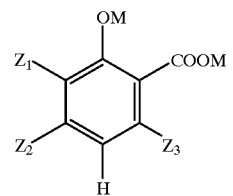

wherein, in said formulae (III) and (IV):

M represents a hydrogen atom, a metallic cation from group (Ia) or (IIa), or an ammonium cation; and $Z_1$, $Z_2$ and $Z_3$, which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group.

24. A process according to claim 23, wherein said acid is decarboxylated by addition of a protonic inorganic or organic acid, until a pH of no more than 3 is obtained.

25. A process according to claim 24, wherein step b), further comprising heating the mixture to be decarboxylated to a temperature of between 120° C. and 350° C., cooling said mixture, and separating the 4-hydroxybenzaldehyde which has the following formula (VI):

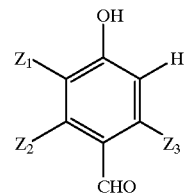

in which formula (VI):

$Z_1$, $Z_2$ and $Z_3$ which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group.

26. A mixture of phenolic compounds which are completely or partially in their salt form, comprising:

a phenolic compound (A) carrying formyl or hydroxymethyl groups in the 2 and 4 position;

a phenolic compound (B) carrying a formyl group or a hydroxymethyl group in the 4 position; and a phenolic compound (C) carrying a formyl or a hydroxymethyl group in the 2 position.

27. A mixture of phenolic compounds having general formula (II):

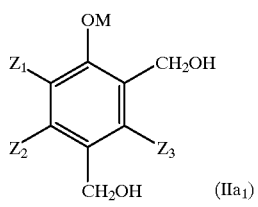

(II)

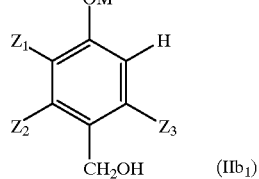

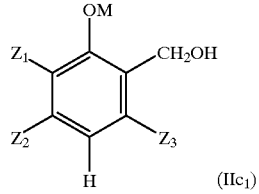

wherein:
M represents a hydrogen atom, a metallic cation from group (Ia) or (IIa), or an ammonium cation; and
$Z_1$, $Z_2$ and $Z_3$ which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group.

28. A mixture of phenolic compounds having general formula (II'):

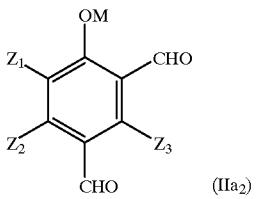

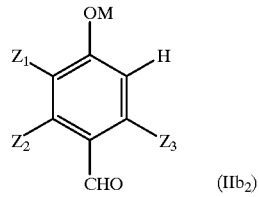

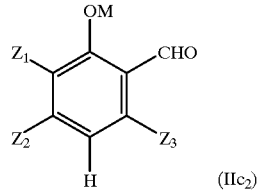

in which formulae:
M represents a hydrogen atom, a metallic cation from group (Ia) or (IIa), or an ammonium cation; and
$Z_1$, $Z_2$ and $Z_3$ which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group.

29. A mixture of phenolic compounds according to claim 26, comprises:
30% to 70% by weight, of the phenolic compound (A);
30% to 70% of a mixture of phenolic compounds (B+C).

30. A process for the preparation of a mixture of phenolic compounds as defined in claim 26, comprising the steps of:
1) hydroxymethylating a phenol by condensing it with formaldehyde or a formaldehyde generator in an aqueous phase in the presence of an alkaline or alkaline-earth base in order to obtain a degree of conversion of phenol of at most 95%, and, then,
2) optionally, carrying out an oxidation step.

31. A process according to claim 30, wherein the degree of phenol conversion is 80% to 95%.

32. A process according to claim 30, wherein the starting phenol is a phenol which is not substituted in the ortho and para positions with respect to the hydroxyl group, with general formula (I):

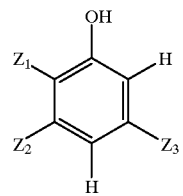

wherein $Z_1$, $Z_2$ and $Z_3$ which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group.

33. A process according to claim 32, wherein the phenol with formula (I) is guaiacol, guetol, 3-methoxyphenol, 3-ethoxyphenol, 3-isopropoxyphenol, 3-t-butoxyphenol, m-cresol, or o-cresol.

34. A process according to claim 30, wherein formaldehyde or formaldehyde generator is trioxane or paraformaldehyde, in the form of a linear polyformaldehyde containing 8 to 100 ($CH_2O$) units.

35. A process according to claim 34, wherein step 1) is carried out with a formaldehyde/phenol molar ratio of between 1.0 and 4.0.

36. A process according to claim 30, wherein the quantity of base present in the hydroxymethylation medium, expressed as a number of moles of base/phenolic hydroxy group of the phenol to be hydroxymethylated, is between 1.0 and 4.0.

37. A process according to claim 30, wherein the hydroxymethylation is carried out at a temperature in the range 0° C. to 100° C.

38. A process according to claim 30, wherein the hydroxymethylation is carried out between 15 minutes and 4 hours.

39. A process for the preparation of a mixture of compounds with formula ($IIa_2$) to ($IIc_2$):

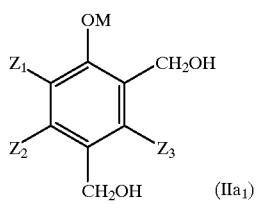

(II)

(IIa₁)

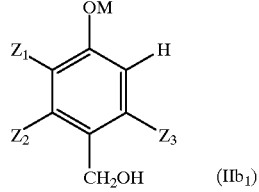

(IIb₁)

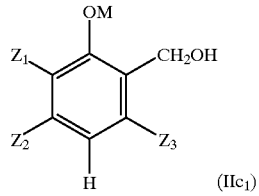

(IIc₁)

wherein:

M represents a hydrogen atom, a metallic cation from group (Ia) or (IIa), or an ammonium cation; and $Z_1$, $Z_2$ and $Z_3$ which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group, said process comprising the steps of:

a) oxidizing hydroxymethylated phenolic compounds with formula (IIa₁) to (IIc₁)

(II')

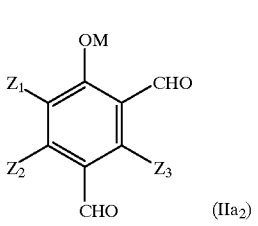

(IIa₂)

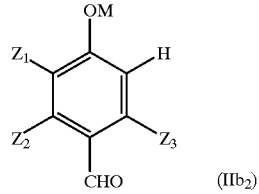

(IIb₂)

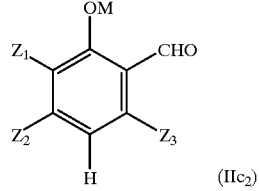

(IIc₂)

in which formulae:

M represents a hydrogen atom, a metallic cation from group (Ia) or (IIa), or an ammonium cation; and $Z_1$, $Z_2$ and $Z_3$ which are identical or different, represent a hydrogen atom, an alkyl, alkenyl, alkoxy, hydroxyalkyl, alkoxyalkyl, cycloalkyl, aryl radical, a hydroxy group, a nitro group, a halogen atom, or a trifluoromethyl group, by using molecular oxygen or a gas containing molecular oxygen, in an aqueous alkaline phase in the presence of a catalyst which is a metal from group 8 of the periodic table, and optionally containing cadmium, cerium, bismuth, lead, silver, tellurium or tin as an activator.

40. A process according to claim 39, wherein the pH of the solution is brought to a value in the range 8 to 13 by optional addition of an alkaline or alkaline-earth base.

41. A process according to claim 39, wherein the temperature of the oxidation reaction is in the range 10° C. to 100° C.

42. A process according to claim 39, wherein the mixture of phenolic compounds with formula (IIa₂) to (IIc₂) is obtained by a two-step process comprising:

hydroxymethylation of a phenol in an aqueous medium in the presence of an alkaline or alkaline-earth base using formaldehyde or a formaldehyde generator resulting in a mixture of hydroxymethylated phenolic compounds, one being hydroxymethylated in the 2 and 4 positions and the two others being hydroxymethylated in the 2 or in the 4 position; and oxidation, without intermediate separation, of the phenolic compounds obtained using molecular oxygen or a gas containing molecular oxygen, in an aqueous alkaline phase in the presence of a catalyst which is a metal from group 8 of the periodic table, and optionally, a metal acting as an activator.

43. A process for the preparation of vanillin according to claim 1, wherein a mixture of phenolic compounds, 4,6-di (hydroxymethyl)guaiacol (A), p-hydroxymethylguaiacol (B) and o-hydroxymethylguaiacol (C) is selectively oxidised at the hydroxymethyl group in the 2-position of compounds (A) and (C) to a carboxy group, and at the hydroxymethyl group in the 4 position in compounds (A) and (B) to a formyl group, resulting in a mixture of 3-carboxy-4-hydroxy-5-methoxybenzaldehyde, vanillin and 2-hydroxy-3-methoxybenzoic acid which, after decarboxylation, produces vanillin and guaiacol which can be recycled.

44. A process for the preparation of vanillin according to claim 1, wherein a mixture of phenolic compounds, 4,6-di (formyl)guaiacol (A), p-formylguaiacol (B) and o-formylguaiacol (C) is selectively oxidised at the formyl group in the 2-position of compounds (A) and (C) to a carboxy group, resulting in a mixture of 3-carboxy-4-hydroxy-5-methoxybenzaldehyde, vanillin and 2-hydroxy-3-methoxybenzoic acid which, after decarboxylation, produces vanillin and guaiacol which can be recycled.

45. A process for the preparation of ethylvanillin according to claim 1, wherein a mixture of phenolic compounds, 4,6-di(hydroxymethyl)guetol (A), p-hydroxymethylguetol (B) and o-hydroxymethylguetol (C) is selectively oxidized at the hydroxymethyl group in the 2-position of compounds (A) and (C) to a carboxy group, and at the hydroxymethyl group in the 4 position in compounds (A) and (B) to a formyl group, resulting in a mixture of 3-carboxy-4-hydroxy-5-ethoxybenzaldehyde, ethylvanillin and 2-hydroxy-3-ethoxybenzoic acid which, after decarboxylation, produces ethylvanillin and guetol which can be recycled.

46. A process for the preparation of ethylvanillin according to claim 1, wherein a mixture of phenolic compounds, 4,6-di(formyl)guetol (A), p-formylguetol (B) and o-formylguetol (C) is selectively oxidized at the formyl group in the 2-position of compounds (A) and (C) to a carboxy group, resulting in a mixture of 3-carboxy-4-hydroxy-5-ethoxybenzaldehyde, ethylvanillin and 2-hydroxy-3-ethoxybenzoic acid which, after decarboxylation, produces ethylvanillin and guetol which can be recycled.

* * * * *